United States Patent
Nguyen-Thien-Nhon

(10) Patent No.: US 6,342,070 B1
(45) Date of Patent: *Jan. 29, 2002

(54) STENTLESS BIOPROSTHETIC HEART VALVE WITH PATENT CORONARY PROTUBERANCES AND METHOD OF SURGICAL USE THEREOF

(75) Inventor: Diana Nguyen-Thien-Nhon, Santa Ana, CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/461,304

(22) Filed: Dec. 14, 1999

Related U.S. Application Data

(63) Continuation of application No. 08/998,318, filed on Dec. 24, 1997, now Pat. No. 6,001,126.

(51) Int. Cl.⁷ .................................................. A61F 2/24
(52) U.S. Cl. ..................................... 623/2.15; 623/1.26
(58) Field of Search ........................ 623/2.1, 2.12–2.19, 623/1.24, 1.26

(56) References Cited

U.S. PATENT DOCUMENTS

| | | |
|---|---|---|
| 3,409,013 A | 11/1968 | Berry |
| 3,548,418 A | 12/1970 | Angell et al. |
| 4,056,854 A | 11/1977 | Boretos et al. |
| 4,182,446 A | 1/1980 | Penny |
| 4,185,636 A | 1/1980 | Gabbay et al. |
| 4,372,743 A | 2/1983 | Lane |
| 4,702,250 A | 10/1987 | Ovil et al. |
| 4,865,600 A | 9/1989 | Carpentier et al. |
| 5,041,131 A | 8/1991 | Nagase |
| 5,089,015 A | 2/1992 | Ross |
| 5,197,979 A | 3/1993 | Quintero et al. |
| 5,279,612 A | 1/1994 | Eberhardt |
| 5,449,384 A | 9/1995 | Johnson |
| 5,769,780 A | 6/1998 | Hata et al. |

FOREIGN PATENT DOCUMENTS

| | | |
|---|---|---|
| EP | 0 073 624 | 3/1983 |
| EP | 0 165 622 | 12/1985 |
| EP | 0 402 036 | 12/1990 |
| GB | 2 108 393 | 5/1983 |
| IT | 1167328 | 5/1987 |
| WO | WO 84/01894 | 5/1984 |
| WO | WO 93/04643 | 3/1993 |
| WO | WO 95/14443 | 6/1995 |
| WO | WO 96/40012 | 12/1996 |

OTHER PUBLICATIONS

D. F. Del Rizzo, et al., "Initial Clinical Experience with the Toronto Stentless Procine Valve™", Journal of Cardiac Surgery, vol. 9, 379–385, 1994.

(List continued on next page.)

*Primary Examiner*—David H. Willse
(74) *Attorney, Agent, or Firm*—Debra D. Condino; John Christopher James; Guy L. Cumberbatch

(57) ABSTRACT

A stentless aortic bioprosthesis having patent, non-ligated coronary artery segments extending therefrom, and methods for surgical replacement of aortic and/or non-aortic (e.g., pulmonary) heart valves with such stentless aortic bioprosthesis. The presence of the patent, non-ligated coronary segments facilitates end to end anastomosis of the patient's native coronary arteries and/or existing coronary artery bypass grafts to the coronary segments of the bioprosthesis even when such native coronary arteries (or coronary grafts) are too short to reach the wall of the aortic segment of the bioprosthesis. The presence of such patent, non-ligated coronary segments also eliminates the need for removal of a "button" or segment of the native aorta in connection with the native coronary artery segments prior to implantation of the bioprosthesis, and is thus advantageous for patients whose ascending aorta is diseased or otherwise compromised.

20 Claims, 3 Drawing Sheets

OTHER PUBLICATIONS

M. Höfig, et al., "Sugery for Acquired Heart Disease: Performance of a Stentless Xenograft Aortic Bioprosthesis up to Four Years After Implantation", The Journal of Thoracic and Cardiovascular Surgery, vol. 103, No. 6, 1068–1073, Jun. 1992.

T. E. David, et al., "Aortic Valve Replacement with Stentless Porcine Bioprostheses ", Journal of Cardiac Surgery, vol. 3, No. 4, 501–505, Dec. 1988.

T. E. David, et al., "Aortic Valve Replacement with Stentless Porcine Aortic Bioprosthesis ", The Journal of Thoracic and Cardiovascular Surgery, vol. 99, No. 1, 113–118, Jan. 1990.

Medtronic, Inc. Brochure for the "Freestyle® Aortic Root Bioprosthesis Implant ", 1995.

St. Jude Medical, Inc. Brochure for "The Toronto SPV™ Stentless Bioprosthesis", 1993.

Baxter Edwards AG, Edwards CVS Division Brochure "Edwards Prima™ Stentless Bioprosthesis", 1995.

Baxter Edwards AG, Edwards CVS Division Brochure "Edwards Prima™ Stentless Bioprosthesis Modified Model 2500 ", 1996.

The Society of Thoracic Surgeons, 1995,—"Aotic Valve Replacement with the Freestyle Stentless Xenograft"; Stephen Westaby; pp. 60–S422–S427; Ann Thorac Surg.

The Society of Thoracic Surgeons , 1995—"Time–Related Hemodydnamic Changes After Aortic Replacement with the Freestyle Stentless Xenograft"; Stephen Westaby; pp. 60:1633–1639: Ann Thorac Surg.

The Society of Thoracic Surgeons, 1995—"Comparison of Implantation Techniques Using Freestyle Stentless Porcine Aortic Valve"; Neal D. Kon, MD; pp. 59:857–862: Am Thorac Surg.

European Journal of Cardio–Thoracic Surgery , 1997—"Stentless porcine bioprostheses for all types of aortic root pathology"; A. Sidiropoulos; pp. 917–921.

Medtronic Brochure —The Freestyle Aortic Root Bioprosthesis; 1993.

Kay et al., "Evolution of Aortic Valvular Prostheses," Journal of Thoracic and Cardiovascular Surgery (45) 3:372–381, Mar. 1963.

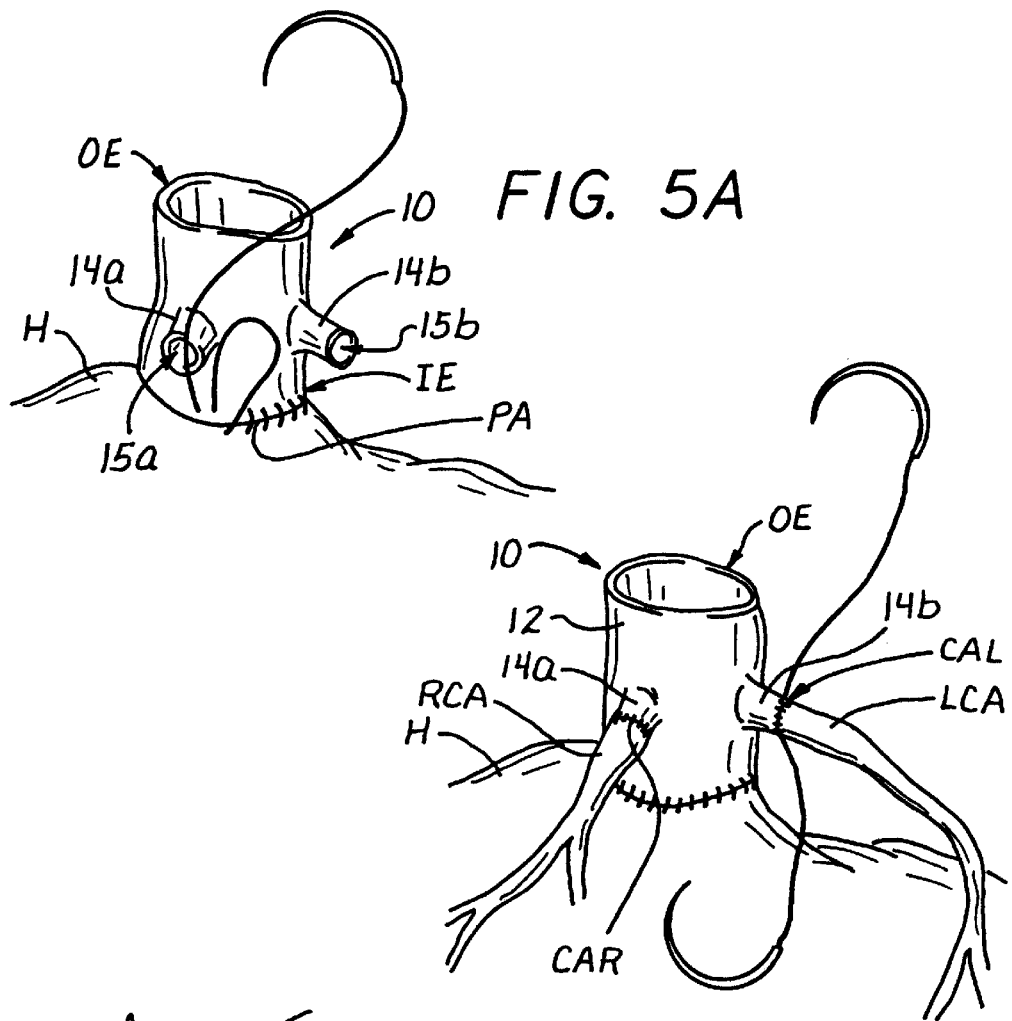
FIG. 5A
FIG. 5B
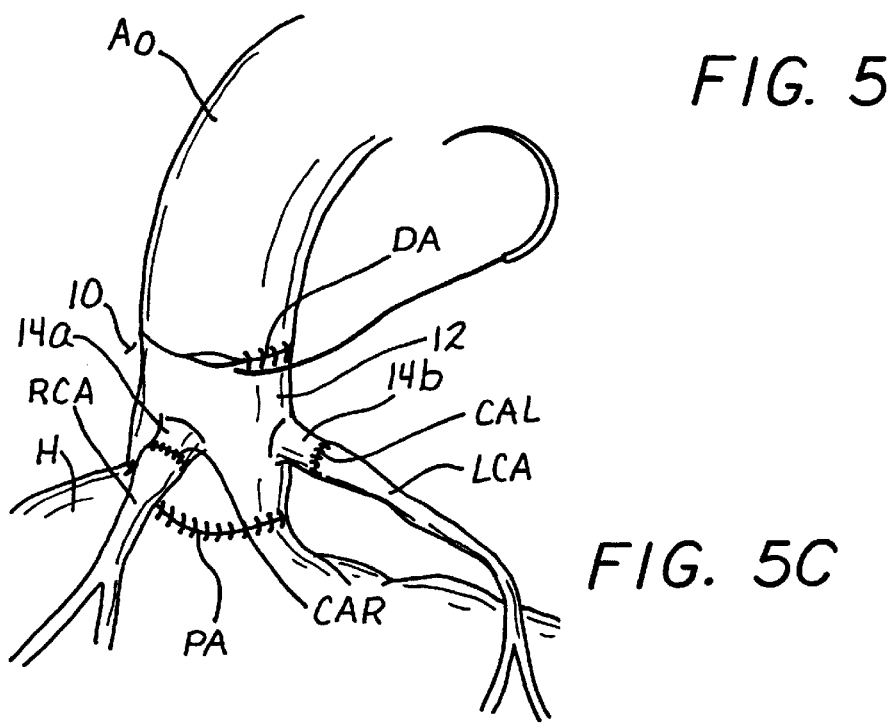
FIG. 5C

STENTLESS BIOPROSTHETIC HEART VALVE WITH PATENT CORONARY PROTUBERANCES AND METHOD OF SURGICAL USE THEREOF

This is a continuation of application Ser. No. 08/998,318, filed on Dec. 24, 1997, now U.S. Pat. No. 6,001,126.

FIELD OF INVENTION

The present invention pertains generally to medical devices and methods, and more particularly to a bioprosthetic heart valve device and related methods for surgical implantation of such bioprosthetic device.

BACKGROUND OF THE INVENTION

Heart valve replacement surgeries have been performed in human beings for many years. Most frequently, these valve replacement procedures are utilized to replace the mitral or aortic valves of patients who suffer from valvular heart disease.

In particular, surgical replacement of the aortic valve has proven to be a successful mode of treatment of patients who are diagnosed with a) obstruction (i.e., stenosis) of the aortic valve or b) leakage (i.e., regurgitation, incompetence or insufficiency) of the aortic valve. In some patients, symptoms of both obstruction and leakage are present, this being known as "mixed disease" or "combined lesions". These types of aortic valvular heart disease may be caused by a number of factors, including congenital deformations, infections, degenerative calcification, and certain rheumatological disorders.

Surgical replacement of the aortic valve is typically performed under general anesthesia, with full cardiopulmonary bypass. An incision is made in the aorta adjacent to the heart, and the leaflets of the endogenous aortic valve are removed along with any calcified surrounding tissue, thereby creating an annular opening (i.e. the "aortic annulus") at the site previously occupied by the endogenous aortic valve. Thereafter, a prosthetic aortic valve is selected and sutured into the aortic annulus, as a prosthetic replacement for the surgically-removed endogenous valve.

The available types of prosthetic aortic valves have heretofore included mechanical valves as well as valves formed of preserved animal tissue (i.e., "bioprosthetic" valves). Of the bioprosthetic valves, some (known as "stented" bioprosthetic valves) incorporate a man-made stent or support frame upon which the preserved biological tissue is mounted. Others (known as "stentless" bioprosthetic valves) do not include any man-made stent or support frame, and are formed entirely of preserved biological tissue.

Tissues for use in bioprosthetic heart valves are typically harvested from the hearts of donor animals and such tissues typically contain large amounts of connective tissue proteins (e.g., collagen and elastin). After the desired tissues have been harvested from the donor animals, they undergo a chemical "fixing" process wherein the connective tissue proteins within the tissue are exposed to one or more chemical cross linking agents capable of forming chemical cross linkages between amino groups present on the connective tissue protein molecules. The types of chemical cross linking agents useable for this purpose include: formaldehyde, glutaraldehyde, dialdehyde starch, hexamethylene diisocyanate and certain polyepoxy compounds.

Examples of commercially available stented bioprosthetic valves include the Carpentier-Edwards®, PERIMOUNT™ Pericardial Bioprosthesis (Baxter Healthcare Corporation, Edwards CVS Division, Post Office Box 11150, Santa Ana, Calif. 92711-1150) as well as the Carpentier-Edwards® Porcine Bioprosthesis (Baxter Healthcare Corporation, Edwards CVS Division, Post Office Box 11150, Santa Ana, Calif. 92711-1150).

Examples of commercially available stentless bioprosthetic valves include the Edwards Prima™ Stentless Bioprosthesis (Baxter Edwards A G, Spierstrasse 5, CH-6848 Horw, Switzerland), the Medtronic Freestyle™ Aortic Root Bioprosthesis (Medtronic, Inc. 7000 Central Avenue NE, Minneapolis, Minn. 55432-3576) and the St. Jude Toronto™ SPV Stentless Bioprosthesis (St. Jude Medical, Inc. One Lillehei Plaza, St. Paul, Minn. 55117).

The stentless bioprosthetic valves may offer superior hemodynamic performance when compared to their stented counterparts, due to the absence of flow restrictions which can be created by the presence of a stent and/or sewing ring. Also, the stentless bioprosthetic valves may exhibit better post-implantation durability than the stented bioprosthetic valves, because they provide a more flexible structure which serves to dissipate stress during the cardiac cycle.

At least one of the previously available aortic bioprostheses (i.e., the Medtronic Freestyle™ Aortic Root Bioprosthesis referred to hereabove) has included a segment of the donor animal's ascending aorta, along with ligated remnants of the donor's coronary arteries extending outwardly therefrom. However, because the coronary artery remnants included in this bioprosthesis have been ligated prior to fixation, the lumens of these coronary artery segments are substantially collapsed and occluded. As a result, it is typically necessary for the surgeon to trim away a substantial portion of each coronary artery remnant, prior to anastomosis of the patient's endogenous coronary arteries thereto.

It is desirable to devise a new stentless aortic bioprosthesis which includes coronary artery remnants which have been fixed in an unligated, natural configuration, such that the lumens of such coronary artery remnants remain patent, and the patient's endogenous coronary arteries may be anastomosed directly thereto.

SUMMARY OF THE INVENTION

The present invention is a stentless aortic bioprosthesis having patent coronary artery protuberances, and related methods for surgical implantation of such bioprosthesis.

In accordance with the invention, there is provided a stentless heart valve bioprosthesis formed of fixed biological tissue, comprising a segment of mammalian aorta having an aortic lumen extending longitudinally therethrough, an inflow end, an outflow end, a plurality of aortic valve leaflets disposed within the aortic lumen. The bioprosthesis includes right and left coronary sinuses, a non-coronary sinus which is situated adjacent to and between the coronary sinuses, and right and left coronary artery segments having coronary artery segment lumens extending therethrough. The coronary artery segments extend outwardly from the coronary sinuses, and the segment of mammalian aorta is fixed with the right and left coronary artery segments defining patent lumens therethrough such that some of the blood which enters the lumen of the aortic segment may flow outwardly through the coronary lumens.

Further in accordance with the invention, mandrel members such as short segments of plastic tubing may be inserted into the lumens of the coronary artery segments, prior to tanning of the tissue, to maintain the patency of the lumens of the coronary artery segments. Ligatures may be tied about the coronary artery segments to hold the mandrel members in place during the tanning (i.e., chemical fixation) process. The mandrel members and any accompanying ligatures may then be removed after completion of the tanning process.

Still further in accordance with the invention, there is provided a method of surgical implantation of an aortic bioprosthesis of the foregoing character to effect a "total root" aortic valve replacement. Such method generally comprises the steps of:

1. surgically transecting the patient's right and left coronary arteries at locations which are spaced distances away from the wall of the patient's ascending aorta;
2. surgically removing a segment of the patient's ascending aorta, along with at least the leaflets of the endogenous aortic valve;
3. anastomosing the aortic bioprosthesis to the patient's native tissues such that the aortic bioprosthesis replaces the removed segment of the ascending aorta; and,
4. either, a) anastomosing the patient's native coronary arteries (or coronary artery bypass grafts) to the coronary segments of the bioprosthesis, at spaced distances from the wall of the aortic segment of the bioprosthesis or b) ligating or otherwise closing the lumens of the coronary segments and attaching the coronary patient's native coronary arteries (or coronary artery bypass grafts) at other locations as may be desirable in certain patients.

Still further in accordance with the invention, there is provided a method of surgical implantation of an aortic bioprosthesis of the foregoing character to effect replacement of a defective pulmonary valve. Such method generally comprises the steps of:

1. surgically removing the patient's pulmonary valve along with an adjacent segment of the pulmonary artery;
2. closing (e.g., ligating, embolizing or placing purse string sutures in) the coronary segments of the bioprosthesis to prevent leakage of blood out of the lumens of such coronary segments; and,
3. anastomosing the aortic bioprosthesis to the patient's native tissues such that the aortic bioprosthesis replaces the removed pulmonary valve and adjacent segment of pulmonary artery.

Still further in accordance with the present invention, there are provided methods of using the aortic bioprosthesis of the foregoing character to effect "mini-root" or "sub-coronary" replacement of a malfunctioning aortic valve. Such mini-root and sub-coronary aortic applications of the bioprosthesis are carried out in accordance with known techniques, by selectively cutting away distal portion(s) of the bioprosthesis and using the remaining portion of the bioprosthesis to carry out a mini-root or sub-coronary aortic implantation procedure.

Further aspects and elements of the present invention will become apparent to those skilled in the art, upon reading and understanding of the detailed description which follows, and viewing of the accompanying drawings.

BRIEF DESCRIPTION OF THE DRAWINGS

FIGS. 5a–5c are step-wise illustrations of a preferred technique for performing a full-root replacement of a defective aortic valve with a stentless aortic bioprosthesis of the present invention.

DESCRIPTION OF THE PREFERRED EMBODIMENTS

Figure 1:
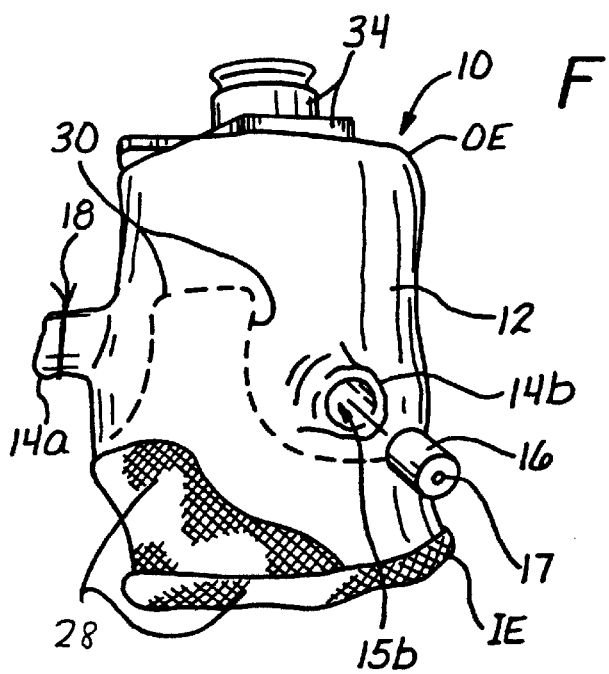
FIG. 1 is a side perspective view of a stentless aortic bioprosthesis of the present invention having a handle-connection fixture mounted on the outflow end thereof.
Figure 2:
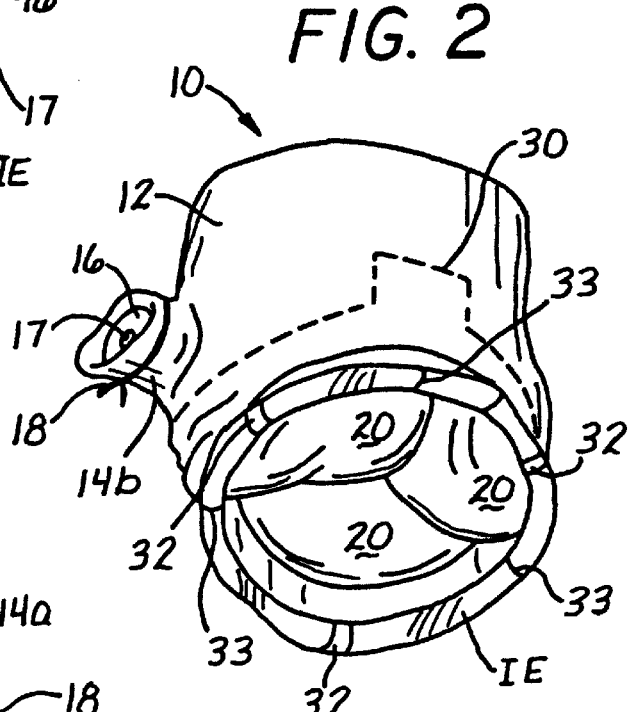
FIG. 2 is a bottom perspective view of the stentless aortic bioprosthesis of FIG. 1.

A. The Preferred Aortic Bioprosthesis having Coronary Protuberances

Turning now to FIGS. 1–4 of the drawings, there is seen a stentless aortic bioprosthesis 10 in accordance with this invention. This aortic bioprosthesis 10 is formed of a preserved segment of mammalian aorta 12 having an inflow rim or inflow end IE, an outflow rim or outflow end OE and the donor animal's aortic valve leaflets 20 positioned therewithin. Segments of the donor animal's right and left main coronary arteries 14a, 14b extend from the aortic segment 12, and such coronary artery segments 14a, 14b have open, patent lumens extending therethrough.

The aortic bioprosthesis 10 of the present invention is preferably of porcine origin. After the tissue of which the bioprosthesis is formed has been harvested from the donor animal, the coronary artery segments 14a, 14b are trimmed to a desired length, such as 1–6 mm and preferably as long as possible (i.e., up to the first coronary bifurcation present on each main coronary artery of the donor animal). Thereafter internal or external support members are inserted or attached to the coronary segments 14a, 14b to maintain patency of the coronary segment lumens 15a, 15b during subsequent tanning. Examples of internal supports which may be used to maintain such patency of the coronary segment lumens 15a, 15b are mandrel members 16 which are sized and configured to be inserted into the lumens 15a, 15b of the coronary artery segments 14a, 14b, as shown in FIG. 1. Such mandrel members 16 may comprise solid members of generally cylindrical configuration, or may comprise segments of tubular members as specifically shown in the drawings, such tubular members having bores 17 extending longitudinally therethrough. The presence of such bores 17 in the tubular mandrel members 16 can be used as passageways for pins or support members which are used to hold or suspend the bioprosthesis 10 during the tanning process. In instances where internal mandrel members 16 are used to maintain patency of the coronary lumens 15a, 15b, ligatures 18 may be tied about the coronary artery segments 14a, 14b following insertion of the mandrel members 16 therein, to frictionally retain the mandrel members 16 within the coronary artery segments 14a, 14b. In the preferred embodiment shown in the drawings the mandrel members 16 are formed of silicone tubing, but they may be formed of other materials such as polyurethane, polyester, polytetraflouroethylene (PTFE), polyethylene, stainless steel, titanium or a metal alloy.

The bioprosthesis 10 having the mandrel members 16 inserted in its coronary segments 14a, 14b is then exposed to a chemical agent (i.e., a fixative agent or tanning agent) which will form chemical cross linkages between connective tissue protein molecules present in the tissue of the bioprosthesis 10. The chemical tanning agents which are useable for this purpose, formaldehyde, dialdehyde starch, hexamethylene diisocyanate and certain polyepoxy compound(s), as well as combinations of these agents. The presently preferred embodiment, shown in the drawings, is by immersion in a solution of 0.625% HEPES buffered glutaraldehyde at pressures of less than approximately 10 mmHg, as described in detail in U.S. Pat. No. 5,800,531, entitled System, Apparatus and Method for Chemical Fixation of Stentless Cardiac Valvular Bioprostheses, which is hereby expressly incorporated by reference.

After the tanning process is complete, the bioprosthesis 10 is removed from the tanning solution and the internal or external support members (e.g., mandrel members 16) are removed. As specifically shown in FIG. 4, in applications wherein internal support members such as the mandrel members 16 have been secured by ligatures 18, such ligatures 18 will typically be removed prior to extraction of the mandrel members 16. Thereafter, if necessary, any distal portions 19 of coronary artery segments 14a, 14b of length $L_2$ located beneath or distal to the ligatures 18 may be cut away and discarded, so as to leave remaining coronary segments 14a, 14b of length $L_1$ and of substantially normal anatomical configuration attached to the bioprosthesis 10. In this regard, it is desirable that such ligatures 18 be placed as distal as possible, so as to maximize the length $L_1$ of the coronary artery segments 14a, 14b which remain after the distal coronary segments 19 have been cut away and discarded. Preferably, the length $L_1$ of the coronary artery segments remaining after final trimming will be at least 2 mm and typically in the range of 2–6 mm, while the length $L_2$ of the discarded distal coronary segments 19 is preferably less than 5 mm.

After the internal or external support members (e.g., mandrels 16) have been removed and the coronary artery segments 14a, 14b have undergone final trimming (if necessary), the bioprosthesis 10 is sterilized by a suitable technique, such as immersion in a biocompatible sterilization solution. The bioprosthesis is then measured to determine its outside diameter, usually rounded off to the nearest millimeter. For commercial applications, bioprostheses 10 which have outside diameters which would round off to an odd number of millimeters (e.g., 15, 17, 19, 21, 23, 25 , 27 and 29 mm) may be rejected.

After the bioprosthesis 10 has been sized, it is subjected to a second trimming step in which substantially all of the myocardial tissue is shaved away, leaving a thin cartilage rim adjacent to the right coronary septal shelf for reinforcement. The left and right coronary artery segments 14a, 14b are allowed to remain. All trimming is conducted with the goal of leaving an intact aortic wall segment above the protruding coronary segments 14a, 14b, such intact aortic wall segment being of sufficient width to a) maintain proper alignment of the commissure, b) prevent distortion of the bioprosthesis 10 during suturing, and/or c) permit replacement of a supracoronary segment of the patient's ascending aorta (e.g., a "total root replacement") if so desired.

Figure 3A:
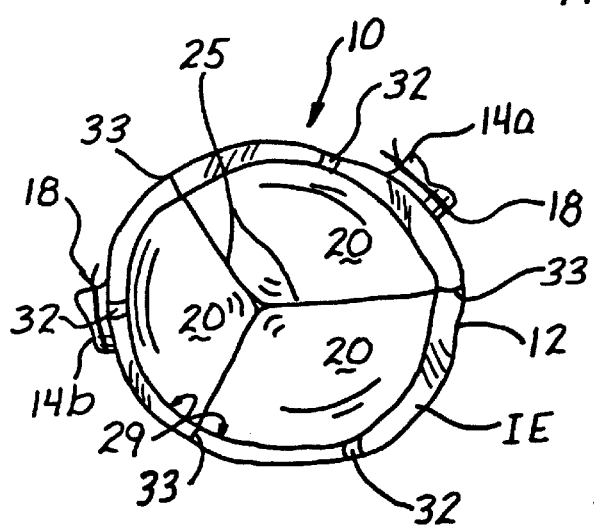
FIG. 3a is a plan view of the inflow end of a stentless aortic bioprosthesis of the present invention.
Figure 3B:
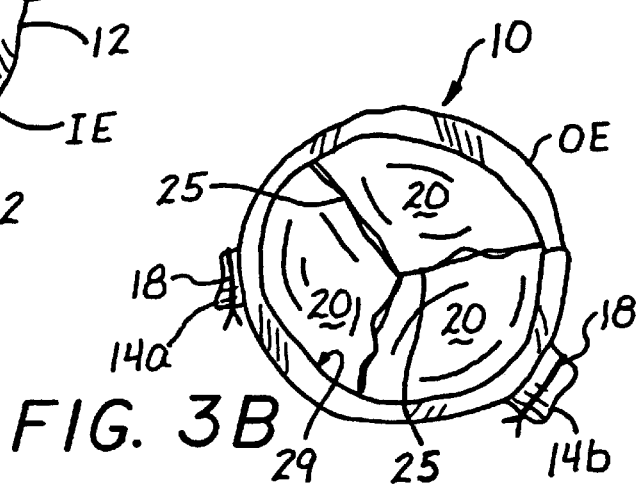
FIG. 3b is a plan view of the outflow end of a stentless aortic bioprosthesis of the present invention.

Finally, the inflow end IE of the bioprosthesis 10 is trimmed on the same plane as the cusps of the valve leaflets 20, usually leaving an intact segment of about 3 to 4 mm in width as measured from the hinge of the leaflet. All of the fatty tissue in the aorta is trimmed away. As shown in FIGS. 3a and 3b, the resulting aortic segment contains three valve leaflets 20, each of which is affixed to the aortic segment at a juncture. The inner edges 25 of the valve leaflets 20 meet when the leaflets 20 are in their closed positions, as shown in the drawings. Also, the leaflets 20 form commissures at their junctions with the aortic wall, and the leaflets are joined to the aortic segment 12 along a leaflet junctures 29. The wall of the aortic segment 12 adjacent junctures 29 forms the Sinus of Valsalva (not shown). The leaflet 20 closest to the right coronary artery segment 14a, is positioned somewhat asymmetrically with respect to the other two leaflets 20.

A fabric covering 28 may optionally be disposed about the inflow end IE of the bioprosthesis 10 and/or upon a portion of one side of the bioprosthesis 10 which corresponds to the right coronary septal shelf, as shown in FIG. 1. This fabric covering 28 enhances the strength of the bioprosthesis 10 which is sutured to the native aortic annulus, and thus serves to deter the sutures from tearing through the tissue of the bioprosthesis 10. This fabric covering 28 may be formed of a thin, biocompatible material which is strong enough to hold sutures. For example, such fabric covering 28 may be formed of woven polyester having a thickness of 0.008 inch" and a weight of 72 grams per square meter. The fabric used for the covering 28 is preferably cut on the diagonal to assure a snug fit around curved surfaces. The fabric is then sewn to the bioprosthesis 10 by hand, using a nonabsorbable, biocompatible thread.

Mid-cusp markings 32, such as stitches formed of thread of a color which contrasts with the body of the bioprosthesis 10, may be formed on the fabric covering 28 along the inflow rim, preferably at the mid-cusp point of each leaflet 20, to aid the surgeon in aligning the bioprosthesis 10 with the patient's natural aorta. For instance, if the cloth is white, the markings 32 may be stitches of navy blue thread, and the like. An exemplary light green marking thread is Polyester PTFE-Coated thread of 6.0 size, having a denier of 110–130.

Additional commissure markings 33 may also be formed on the fabric covering and/or inflow end of the bioprosthesis 10 at the locations of the valvular commissures to aid the surgeon in aligning the bioprosthesis with the patient's native anatomical structures. These optional commissure markings 33 may be formed in the same manner as described hereabove with respect to the mid-cusp markings 32, but will preferably of a color which is different from the mid-cusp markings 32 so as to permit the surgeon to easily distinguish between the mid-cusp markings 32 and commissure markings 33.

A valve retainer fixture 34 may be attached to the outflow end OE of the bioprosthesis, as shown, to facilitate the attachment of an elongate handle thereto. Such valve retainer fixture 34 may be of the type described in U.S. Pat. No. 5,336,258 (Quintero et al.). Alternatively, in lieu of the use of such valve retainer fixture 34, the bioprosthesis may be mounted within a cage-like holding apparatus of the type described in copending U.S. patent application Ser. No. 08/723,420, entitled Bioprosthetic Heart Valve Implantation Device.

B. Methods of Implanting the Preferred Aortic Bioprosthesis having Coronary Protuberances:

The currently used methods for surgical implantation of the bioprosthesis 10 of the present invention typically require that the patient be placed under general anesthesia and on cardiopulmonary bypass. An incision is made in the patient's chest wall (e.g., a median sternotomy) and the heart is exposed. The malfunctioning endogenous valve (typically the aortic valve but possibly another cardiac valve such as the pulmonary valve located between the right ventricle and the pulmonary artery) is then removed and the bioprosthesis 10 (or a portion thereof) is sutured into place to act as a prosthetic replacement for the previously-removed endogenous valve.

Figure 4:
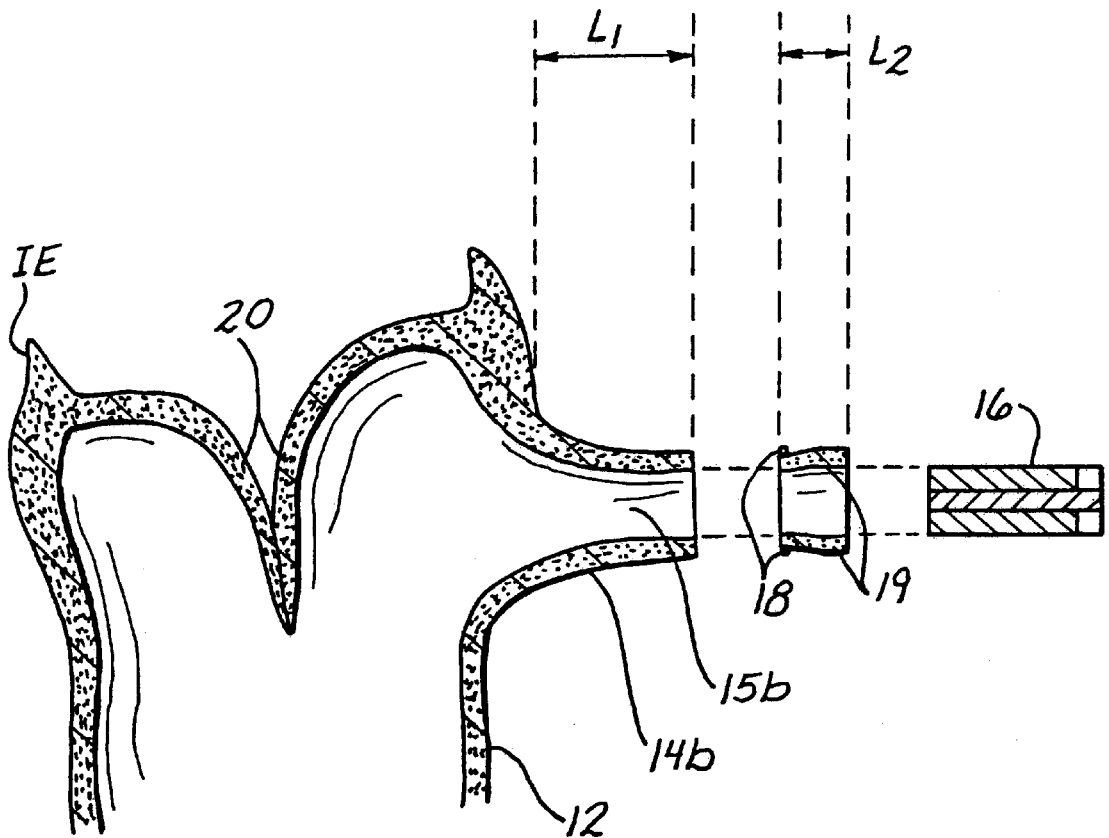
FIG. 4 is a longitudinal section view of the aortic bioprosthesis, through line 4—4 of FIG. 1.
Figure 4A:
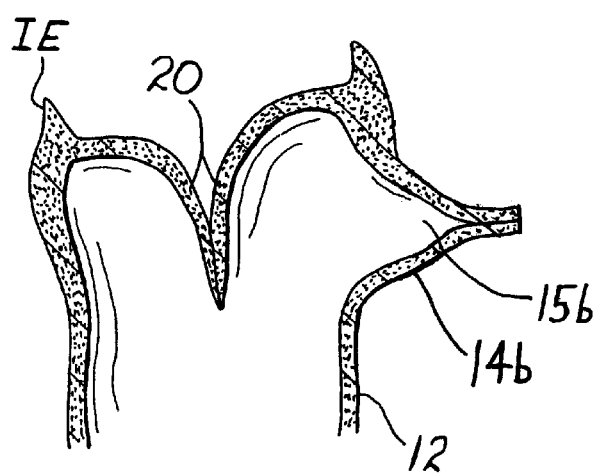
FIG. 4A is a longitudinal section view of the aortic bioprosthesis, as in FIG. 4, and showing a coronary protuberance closed.

The bioprosthesis 10 shown in FIGS. 1–4 will typically be implanted at the aortic position to replace the endogenous aortic heart valve. However, in some instances the bioprosthesis 10 may also be utilized to replace another heart valve such as a malfunctioning pulmonary valve located between the right ventricle and pulmonary artery. When used to replace a heart valve other than the aortic valve, the lumens 15a, 15b of the coronary segments 14a, 14b will typically be closed off (as seen in FIG. 4A) by suitable closure means such as ligation, embolization, or placement of a purse string suture.

i Subtotal Aortic Applications of the Bioprosthesis:

In the mini-root and sub-coronary techniques previously known in the art, a bioprosthesis 10 of appropriate size is selected and is either a) trimmed along marker thread 30 or at some other location selected by the surgeon to separate the aortic root portion of the bioprosthesis 10 (i.e., the base of the aortic segment 12 having the leaflets 20 disposed therein) from the remainder of its aortic segment 12 and coronary segments 14a, 14b or b) the lumens 15 of the coronary segments 14a, 14b are closed by ligation, placement of a purse string suture thereabout, embolization of other suitable means to prevent blood from subsequently leaking out of the lumens 15 of those coronary segments 14a, 14b. Thereafter the bioprosthesis 10 may be implanted at the aortic location to replace the patient's endogenous aortic valve, without attachment of coronary arteries or other vessels or grafts to the coronary segments 14a, 14b.

ii. Total-Root Aortic Applications of the Bioprosthesis:

In other applications, the entire bioprosthesis 10, including the entire aortic segment 12 and coronary artery segments 14a, 14b may be implanted at the aortic location, in accordance with the procedure shown in FIGS. 5a–5c. In this procedure, the patient's right coronary artery RCA and left coronary artery LCA are transected at locations which are spaced distances away from the wall of the patient's ascending aorta AO and a segment of the patient's ascending aorta AO is removed and the native aortic valve leaflets are surgically excised and removed.

A bioprosthesis 10 of correct size is selected, and a handle (not shown) is attached to the handle connection fixture. The handle (not shown) is then used to position the bioprosthesis 10 such that its inflow end IE is in juxtaposition to the aortic annulus, and a proximal anastomosis PA is formed to secure the inflow end IE of the bioprosthesis 10 to the native aortic annulus.

Thereafter, the native right coronary artery RCA is trimmed to length, if necessary, and a right coronary anastomosis CAR is formed between the transected end of the right coronary artery RCA and the distal end of the right coronary segment 14a of the bioprosthesis 10. The native left coronary artery LCA is then trimmed to length, if necessary, and a left coronary anastomosis CAL is formed between the transected end of the left coronary artery LCA and the distal end of the left coronary segment 14b of the bioprosthesis 10. The patient's coronary arterial vasculature is thereby connected to the aortic segment 12 of the bioprosthesis 10 such that a portion of the arterial blood which subsequently flow is into the aortic segment 12 of the bioprosthesis 10 will flow into the right and left main coronary arteries RCA, LCA to perfuse the patient's myocardium in accordance with normal hemodynamics.

In patients where coronary artery bypass graft(s) are present, one of more openings may be made in the aortic segment 12 of the bioprosthesis, and the ends of the bypass graft(s) may be sutured to such openings in accordance with well known surgical technique.

Finally, the outflow end of the handle (not shown) and valve retainer fixture 34 are disconnected and removed, and to end approximation with the outflow end of the bioprosthesis 10. A distal anastomosis DA is then formed therebetween, as shown in FIG. 5c.

Thereafter, the patient may be removed from cardiopulmonary bypass and the chest incision may be closed.

The invention has been described hereabove with reference to certain presently preferred embodiments only, and no attempt has been made to exhaustively describe all possible embodiments of the invention. For example, with respect to the method for implantation of the bioprosthesis 10, it may be possible to accomplish implantation of the bioprosthesis by a minimal access (e.g. "keyhole") technique without the need for forming large incisions in the patient's chest wall, but rather by forming a plurality of small minimal access incisions—and using a thoracoscopic technique to perform the implantation surgery. Accordingly, it is intended that the above-described preferred embodiments as well as all possible other embodiments of the invention be included within the scope of the following claims.

What is claimed is:

1. A stentless heart valve bioprosthesis comprising:
   a fully implantable segment of mammalian aorta having an aortic lumen extending longitudinally therethrough, an inflow end, an outflow end, a plurality of aortic valve leaflets disposed within the aortic lumen, right and left coronary sinuses, a non-coronary sinus which is situated adjacent to and between the coronary sinuses, and right and left coronary artery segments having coronary artery segment lumens extending therethrough, the coronary artery segments extending outwardly from the coronary sinuses, the segment of mammalian aorta having been chemically fixed in such a way that the right and left coronary artery segments have a length of at least 2 mm and define patent lumens therethrough, wherein the coronary artery segments may be anastomosed to the native coronary arteries such that some of the blood which enters the lumen of the aortic segment may flow outwardly through the coronary lumens.

2. The bioprosthesis of claim 1 wherein the bioprosthesis has been formed in a fixing process using support members to maintain patency of the coronary lumens during the fixing process.

3. The bioprosthesis of claim 2 wherein the support members comprise mandrel members which are inserted into the coronary lumens to maintain patency of the coronary lumens during the fixing process.

4. The bioprosthesis of claim 3 wherein the mandrel members are formed of material selected from the group of materials consisting of:
   (a) silicone:
   (b) polyurethane;
   (c) polyester;
   (d) polytetrafluoroethylene;
   (e) polyethylene;
   (f) stainless steel;
   (g) titanium; and,
   (h) a metal alloy.

5. The bioprosthesis of claim 3 wherein the mandrel members have bores extending longitudinally therethrough.

6. The bioprosthesis of claim 3 further comprising;
   mandrel retaining apparatus placed upon the coronary artery segments to hold the mandrel members within the coronary lumens, the mandrel retaining apparatus being removable following fixing of the bioprosthesis.

7. The bioprosthesis of claim 6 wherein the mandrel retaining apparatus are selected from the group of mandrel retaining apparatus consisting of:
ligatures placed about the coronary artery segments; and,
clamps placed upon the coronary artery segments.

8. The bioprosthesis of claim 6 wherein any portion of the coronary artery segments which may have been deformed by the mandrel retaining apparatus is cut away after fixing of the bioprosthesis.

9. The bioprosthesis of claim 8 wherein after any portion of the coronary artery segments which have been deformed by the mandrel retaining apparatus have been cut away, the remaining coronary artery segments are 2–6 mm in length.

10. The bioprosthesis of claim 1 wherein the segment of mammalian aorta is of porcine origin.

11. The bioprosthesis of claim 1 wherein the segment of mammalian aorta has been formed in a chemical fixing process using at least one fixative agent selected from the group of fixative agents consisting of:
an aldehyde;
glutaraldehyde;
formaldehyde:
a polyepoxy compound;
dialdehyde starch;
hexamethylene diisocyanate; and
combinations thereof.

12. The bioprosthesis of claim 1 further comprising:
a fabric reinforcement formed on at least a portion of the bioprosthesis to enhance its strength.

13. The bioprosthesis of claim 12 wherein the reinforcement fabric is formed about the inflow end of the bioprosthesis.

14. The bioprosthesis of claim 1 further comprising:
marker thread visible on the exterior of the segment of mammalian aorta to act as a guide in separating a portion of the bioprosthesis having the leaflets disposed therein from the remainder of the aorta and coronary artery segments.

15. A method of surgical replacement of a heart valve with a bioprosthesis as claimed in claim 1, comprising:
surgically transecting the patient's right and left coronary arteries at locations which are spaced distances away from the wall of the patient's ascending aorta;
surgically removing a segment of the patient's ascending aorta, along with at least the leaflets of the endogenous aortic valve;
anastomosing the bioprosthesis to the patient's native tissues such that the segment of mammalian aorta replaces the removed segment of the ascending aorta; and,
anastomosing at least one of the patient's coronary arteries to the corresponding coronary artery segment of the bioprosthesis at a spaced distance from the segment of mammalian aorta.

16. The method of claim 15 wherein the anastomosis of the patient's coronary artery to the coronary artery segment of the bioprosthesis is located between about 2–6 mm from the segment of mammalian aorta.

17. The method of claim 15 including anastomosing both of the patient's coronary arteries to the coronary artery segments of the bioprosthesis at spaced distances from the segment of mammalian aorta.

18. A method of surgical replacement of a heart valve with a bioprosthesis comprising:
providing a stentless heart valve bioprosthesis comprising a segment of mammalian aorta having an aortic lumen extending longitudinally therethrough, an inflow end, an outflow end, a plurality of aortic valve leaflets disposed within the aortic lumen, right and left coronary sinuses, a non-coronary sinus which is situated adjacent to and between the coronary sinuses, and right and left coronary artery segments having coronary artery segment lumens extending therethrough, the coronary artery segments extending outwardly from the coronary sinuses, the segment of mammalian aorta having been fixed with the right and left coronary artery segments defining patent lumens such that some of the blood which enters the lumen of the aortic segment may flow outwardly through the coronary lumens;
surgically removing the patient's heart valve and a quantity of vascular tissue adjacent to the heart valve;
closing at least one of the patent lumens of the coronary artery segments of the bioprosthesis such that blood which flows through the lumen of the bioprosthesis will not flow out of the closed coronary artery segment; and anastomosing the bioprosthesis to the patient's native tissues such that the aortic bioprosthesis replaces the removed heart valve and adjacent vascular tissue.

19. The method of claim 18 closing both of the patent lumens of the coronary artery segments of the bioprosthesis such that blood which flows through the lumen of the bioprosthesis will not flow out of the closed coronary artery segments.

20. The method of claim 18 wherein the step of closing the patent lumen of the coronary artery segment of the bioprosthesis includes ligating the coronary artery segment.

* * * * *